(12) United States Patent
Mauger et al.

(10) Patent No.: US 7,557,248 B2
(45) Date of Patent: Jul. 7, 2009

(54) METHOD OF FORMING A CARBON-HETEROATOM BOND

(75) Inventors: Christelle Mauger, Oullins (FR); Gérard Mignani, Lyons (FR)

(73) Assignee: Rhodia Chimie, Boulogne Billancourt (FR)

( * ) Notice: Subject to any disclaimer, the term of this patent is extended or adjusted under 35 U.S.C. 154(b) by 133 days.

(21) Appl. No.: 10/556,849

(22) PCT Filed: May 12, 2004

(86) PCT No.: PCT/FR2004/001159

§ 371 (c)(1),
(2), (4) Date: Dec. 20, 2006

(87) PCT Pub. No.: WO2004/101496

PCT Pub. Date: Nov. 25, 2004

(65) Prior Publication Data

US 2007/0243999 A1 Oct. 18, 2007

(30) Foreign Application Priority Data

May 15, 2003 (FR) .................................. 03 05826

(51) Int. Cl.
*C07C 241/00* (2006.01)

(52) U.S. Cl. ...................................................... 564/251
(58) Field of Classification Search ....................... None
See application file for complete search history.

(56) References Cited

U.S. PATENT DOCUMENTS 6,100,398 A * 8/2000 Hartwig et al. ............. 544/264
6,235,936 B1 * 5/2001 Buchwald et al. ........... 564/386

* cited by examiner

*Primary Examiner*—Brian J Davis
(74) *Attorney, Agent, or Firm*—B. Aaron Schulman; Stites & Harbison PLLC

(57) ABSTRACT

The present invention relates to a method of creating a carbon-heteroatom bond, and preferably a carbon-nitrogen bond, by reacting a leaving group-bearing unsaturated compound and a nucleophilic compound. In particular, the invention relates to the creation of a carbon-nitrogen bond, using a method involving the arylation of nitrogenous organic derivatives; the inventive method consists in creating a carbon-heteroatom bond by reacting a leaving group-bearing unsaturated compound and a nucleophilic compound introducing a heteroatom which can be substituted for the leaving group, thereby creating a carbon-heteroatom bond, in the presence of a palladium-based catalyst, optionally a ligand. The invention is characterized in that the reaction takes place in the presence of an effective quantity of a metal hydroxide or ammonium hydroxide which is associated with an alcohol-type solvent.

38 Claims, No Drawings

METHOD OF FORMING A CARBON-HETEROATOM BOND

This application is an application under 35 U.S.C. Section 371 of International Application Number PCT/FR2004/001159 filed on May 12, 2004.

The present invention relates to a method of creating a carbon-heteroatom bond, and preferably a carbon-nitrogen bond, by reacting a leaving group-bearing unsaturated compound and a nucleophilic compound.

The invention relates in particular to the creation of a carbon-nitrogen bond according to a method involving the arylation of nitrogenous organic derivatives.

Many important compounds exist that are used in the agrochemical and pharmaceutical field, for example arylhydrazines or arylhydrazones which result from the arylation of a nitrogenous nucleophilic compound by creation of a carbon-nitrogen bond.

The arylation reactions involve a catalyst and several types of homogeneous or heterogeneous catalysts have been described.

Palladium is commonly used for this reaction. Thus, Buchwald et al. (U.S. Pat. No. 6,235,936) have disclosed a method involving the arylation, vinylation or alkynation of hydrazines, hydrazones, hydroxylamines and oximes, consisting in reacting the nitrogenous compound with an aromatic substrate comprising a carbon activated with a leaving group, in the presence of a transition metal catalyst, optionally a ligand, most commonly a phosphine.

In order to promote the reactivities of the catalyst or the substrate, it may be necessary to introduce a base. Although all types of base are mentioned in the patent cited, it emerges that the only bases exemplified are sodium tert-butoxide or cesium carbonate.

The drawback in using such bases is that they are expensive. In addition, sodium tert-butoxide is not very easy to handle since it is very hygroscopic.

The objective of the present invention is to provide a method that overcomes the abovementioned drawbacks.

A method has now been found, and it is this that constitutes the subject of the present invention, which is a method of creating a carbon-heteroatom bond by reacting a leaving group-bearing unsaturated compound and a nucleophilic compound introducing a heteroatom which can substitute for the leaving group, thereby creating a carbon-heteroatom bond, in the presence of a palladium-based catalyst, optionally a ligand, characterized in that the reaction takes place in the presence of an effective amount of a metal hydroxide or ammonium hydroxide, associated with an alcohol-type solvent.

According to a preferred variant of the method of the invention, the metal hydroxide or ammonium hydroxide and the solvent are introduced, during the reaction, in the form of an alcoholic suspension prepared by reactive milling of the metal hydroxide or ammonium hydroxide and the alcohol.

It has now been found that it is possible to carry out the coupling of an unsaturated substrate and a nucleophilic compound in the presence of a base such as sodium hydroxide provided that the latter is associated with an alcohol-type solvent.

It has also been found that it is not possible to make use of an aprotic organic solvent, in particular of hydrocarbon type, used alone, but that it is suitable once it is mixed with an alcohol-type solvent.

Finally, it has been found that the introduction of an alcoholic suspension of the metal hydroxide or ammonium hydroxide prepared by wet milling makes it possible to accelerate the kinetics of the coupling reaction and makes it possible to decrease the amount of palladium and of ligand associated with the metal used.

Such a method is much more economically advantageous and can be readily transposed to the industrial scale.

According to a first variant of the method of the invention, an arylation reaction is carried out by reacting a leaving group-bearing aromatic compound and a nucleophilic, preferably nitrogenous, compound.

According to another variant of the method of the invention, a vinylation or alkynation reaction is carried out by reacting, respectively, a compound having a double or triple bond in the α-position with respect to a leaving group, and a nucleophilic, preferably nitrogenous, compound.

In the following disclosure of the present invention, the term "arylation" is used with extensive meaning since the use of an aromatic-type compound is envisioned, whether it is carbocyclic or heterocyclic.

The term "aromatic" is intended to mean the conventional notion of aromaticity as defined in the literature, in particular by J. March "Advanced Organic Chemistry", 4th ed., John Wiley & Sons, 1992, pp 40 et seq.

The term "nucleophilic compound" is intended to mean an organic hydrocarbon compound that may be both acyclic and cyclic and the characteristic of which is that it comprises at least one oxygen atom and/or at least one nitrogen atom bearing a free doublet: it being possible for said nitrogen atom to be introduced by means of a functional group, or included in a ring in the form of NH.

Thus, the nucleophilic substrate comprises at least one atom or group below, such as in particular:

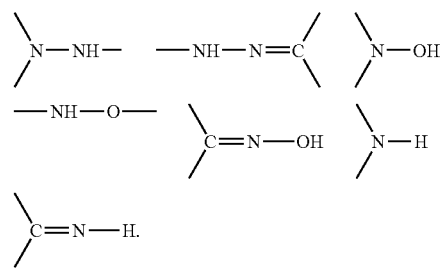

According to another variant of the invention, the nucleophilic compound comprises at least one nitrogen atom bearing a free doublet included in a saturated, unsaturated or aromatic ring: the ring generally comprising from 3 to 8 atoms.

Nucleophilic Compounds

The method of the invention involves a large number of nucleophilic compounds and examples are given hereinafter, by way of illustration and without in any way being limiting in nature.

A first category of substrates to which the method of the invention applies are primary or secondary amines, and imines.

More specifically, the primary or secondary amines can be represented by a general formula:

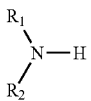

(Ia)

in said formula (Ia):
$R_1$ and $R_2$ represent, independently of one another, a hydrogen atom or a hydrocarbon group having from 1 to 20 carbon atoms, which may be a linear or branched, saturated or unsaturated, acyclic aliphatic group; a monocyclic or polycyclic, saturated, unsaturated or aromatic carbocyclic or heterocyclic group; a chain of the abovementioned groups,
at most one of the groups $R_1$ and $R_2$ represents a hydrogen atom.

In formula (Ia), the various symbols may have more particularly the meaning given hereinafter.

Thus, $R_1$ and $R_2$ may represent, independently of one another, a linear or branched, saturated or unsaturated, acyclic aliphatic group.

More specifically, $R_1$ and $R_2$ preferentially represent a linear or branched, saturated acyclic aliphatic group, preferably $C_1$ to $C_{12}$, and even more preferentially $C_1$ to $C_4$.

The invention does not exclude the presence of an unsaturation on the hydrocarbon chain, such as one or more double bonds which may or may not be conjugated.

The hydrocarbon chain may optionally be interrupted with a heteroatom (for example, oxygen, sulfur, nitrogen or phosphorus) or with a functional group insofar as the latter does not react, and mention may in particular be made of a group such as especially —CO—.

The hydrocarbon chain may optionally bear one or more substituents (for example, halogen, ester, amino or alkyl and/or arylphosphine) insofar as they do not interfere.

The linear or branched, saturated or unsaturated, acyclic aliphatic group may optionally bear a cyclic substituent. The term "ring" is intended to mean a saturated, unsaturated or aromatic, carbocyclic or heterocyclic ring.

The acyclic aliphatic group may be connected to the ring via a valency bond, a heteroatom or a functional group, such as oxy, carbonyl, carboxyl, sulfonyl, etc.

As examples of cyclic substituents, cycloaliphatic, aromatic or heterocyclic substituents may be envisioned, in particular cycloaliphatic substituents comprising 6 carbon atoms in the ring or benzene substituents, these cyclic substituents themselves optionally bearing any substituent insofar as they do not hinder the reactions involved in the method of the invention. Mention may in particular be made of $C_1$ to $C_4$ alkyl or alkoxy groups.

Among the aliphatic groups bearing a cyclic substituent, cycloalkylalkyl, for example cyclohexylalkyl, groups or aralkyl groups, preferably $C_7$ to $C_{12}$ alkyl groups, especially benzyl or phenylethyl, are more particularly targeted.

In general formula (Ia), the groups $R_1$ and $R_2$ may also represent, independently of one another, a saturated carbocyclic group or a carbocyclic group comprising 1 or 2 unsaturations in the ring, which is generally $C_3$ to $C_8$, preferably with 6 carbon atoms in the ring; it being possible for said ring to be substituted. As preferred examples of groups of this type, mention may be made of cyclohexyl groups optionally substituted with linear or branched alkyl groups having from 1 to 4 carbon atoms.

The groups $R_1$ and $R_2$ may represent, independently of one another, an aromatic hydrocarbon group, and in particular a benzene group, corresponding to general formula ($F_1$):

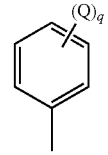

($F_1$)

in which:
q represents an integer from 0 to 5,
Q represents a group chosen from a $C_1$ to $C_6$ linear or branched alkyl group, a $C_1$ to $C_6$ linear or branched alkoxy group, a $C_1$ to $C_6$ linear or branched alkylthio group, an —$NO_2$ group, a —CN group, a halogen atom and a $CF_3$ group.

$R_1$ and $R_2$ may also represent, independently of one another, a polycyclic aromatic hydrocarbon group with it being possible for the rings to form with one another ortho-condensed or ortho- and pericondensed systems. Mention may more particularly be made of a naphthyl group; it being possible for said ring to be substituted.

$R_1$ and $R_2$ may also represent, independently of one another, a polycyclic hydrocarbon group consisting of at least 2 saturated and/or unsaturated carbocycles or of at least 2 carbocycles of which only one is aromatic and which form with one another ortho-condensed or ortho- and pericondensed systems. Generally, the rings are $C_3$ to $C_8$, preferably $C_6$, rings. As more specific examples, mention may be made of the bornyl group or the tetrahydronaphthalene group.

$R_1$ and $R_2$ may also represent, independently of one another, a saturated, unsaturated or aromatic heterocyclic group containing in particular 5 or 6 atoms in the ring, including one or two heteroatoms such as nitrogen (not substituted with a hydrogen atom), sulfur and oxygen atoms; it being possible for the carbon atoms of this heterocycle to also be substituted.

$R_1$ and $R_2$ may also represent a polycyclic heterocyclic group defined as being either a group consisting of at least two aromatic or nonaromatic heterocycles containing at least one heteroatom in each ring and forming with one another ortho-condensed or ortho- and pericondensed systems, or a group consisting of at least one aromatic or nonaromatic hydrocarbon ring and at least one aromatic or nonaromatic heterocycle forming with one another ortho-condensed or ortho- and pericondensed systems; it being possible for the carbon atoms of said rings to be optionally substituted.

By way of examples of groups $R_1$ and $R_2$ of heterocyclic type, mention may be made, inter alia, of furyl, thienyl, isoxazolyl, furazanyl, isothiazolyl, pyridyl, pyridazinyl, pyrimidinyl, pyranyl and phosphino groups and quinolyl, naphthyridinyl, benzopyranyl and benzofuranyl groups.

The number of substituents present on each ring depends on the carbon condensation of the ring and on the presence or absence of an unsaturation on the ring. The maximum number of substituents that can be borne by a ring is readily determined by those skilled in the art.

The amines used preferentially correspond to formula (Ia) in which $R_1$ and $R_2$, which may be identical or different, represent a $C_1$ to $C_{15}$, preferably $C_1$ to $C_{10}$, alkyl group, a $C_3$ to $C_8$, preferably $C_5$ or $C_6$, cycloalkyl group, or a $C_6$ to $C_{12}$ aryl or arylalkyl group.

As more specific examples of groups $R_1$ and $R_2$, mention may be made of $C_1$ to $C_4$ alkyl, phenyl, benzyl or naphthyl groups.

As more specific examples of amines corresponding to formula (Ia), mention may be made of aniline, N-methylaniline, diphenylamine, benzylamine and dibenzylamine.

As regards the imines, they can be represented by the formula below:

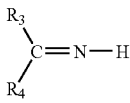
(Ib)

in said formula:
- $R_3$ and $R_4$, which may be identical or different, have the meaning given for $R_1$ and $R_2$ in formula (Ia),
- at most one of the groups $R_3$ and $R_4$ represents a hydrogen atom.

The imines used preferentially correspond to formula (Ib) in which $R_3$ and $R_4$, which may be identical or different, represent a $C_1$ to $C_{15}$, preferably $C_1$ to $C_{10}$, alkyl group, a $C_3$ to $C_8$, preferably $C_5$ or $C_6$, cycloalkyl group, or a $C_6$ to $C_{12}$ aryl or arylalkyl group.

As more specific examples of groups $R_3$ and $R_4$, mention may be made of $C_1$ to $C_4$ alkyl, phenyl, benzyl or naphthyl groups.

Other nucleophiles that can be used in the method of the invention are oximes and hydroxylamines.

The oximes can be represented by the formula below:

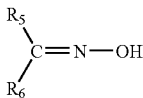
(Ic)

in said formula:
- $R_5$ and $R_6$, which may be identical or different, have the meaning given for $R_1$ and $R_2$ in formula (Ia),
- at most one of the groups $R_5$ and $R_6$ represents a hydrogen atom.

The hydroxylamines can be represented by the formula below:

$$R_7-NH-OR_8 \quad (Id)$$

in said formula:
- $R_7$ has the meaning given for $R_1$ and $R_2$ in formula (Ia) with the exception of a hydrogen atom,
- $R_8$ represents a hydrogen atom, a linear or branched, saturated or unsaturated, acyclic aliphatic group; a monocyclic or polycyclic, saturated or unsaturated carbocyclic group; a chain of the abovementioned groups.

The oximes or hydroxylamines used preferentially correspond to formulae (Ic) or (Id) in which $R_5$, $R_6$ and $R_7$ represent more particularly a $C_1$ to $C_{15}$, preferably $C_1$ to $C_{10}$, alkyl group, a $C_3$ to $C_8$, preferably $C_5$ or $C_6$, cycloalkyl group, or a $C_6$ to $C_{12}$ aryl or arylalkyl group.

As more specific examples of groups $R_5$, $R_6$ and $R_7$, mention may be made of $C_1$ to $C_4$ alkyl, phenyl, benzyl or naphthyl groups.

As regards $R_8$, it is preferentially a $C_1$ to $C_4$ alkyl group or a benzyl group.

The invention is directed more particularly toward the nucleophilic compounds of hydrazine type.

They can be symbolized by the formula below:

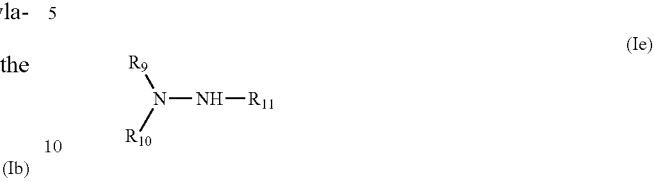
(Ie)

in said formula:
- $R_9$, $R_{10}$ and $R_{11}$, which may be identical or different, have the meaning given for $R_1$ and $R_2$ in formula (Ia).
- $R_{11}$ represents a hydrogen atom or a protective group G,
- at most one of the groups $R_9$ and $R_{10}$ represents a hydrogen atom,
- or else $R_9$ and $R_{10}$ may be linked so as to constitute, with the carbon atoms that bear them, a monocyclic or polycyclic, saturated, unsaturated or aromatic, carbocyclic or heterocyclic group having from 3 to 20 atoms.

The hydrazines used preferentially correspond to formula (Ie) in which $R_9$ and $R_{10}$, which may be identical or different, represent a $C_1$ to $C_{15}$, preferably $C_1$ to $C_{10}$, alkyl group, a $C_3$ to $C_8$, preferably $C_5$ or $C_6$, cycloalkyl group, or a $C_6$ to $C_{12}$ aryl or arylalkyl group.

As more specific examples of groups $R_9$ and $R_{10}$, mention may be made of $C_1$ to $C_4$ alkyl, phenyl, benzyl or naphthyl groups.

$R_9$ and $R_{10}$ may be linked so as to constitute, with the carbon atoms that bear them, a saturated, unsaturated or aromatic, carbocyclic or heterocyclic group having from 3 to 20 atoms, which is monocyclic or polycyclic comprising two or three ortho-condensed rings, which means that at least two rings have two carbon atoms in common. In the case of the polycyclic compounds, the number of atoms in each ring varies preferably between 3 and 6. $R_9$ and $R_{10}$ preferentially form a ring of cyclohexane or fluorenone type.

In formula (Ie), $R_{11}$ represents more particularly a hydrogen atom, a preferably $C_1$ to $C_{12}$ alkyl group; a preferably $C_2$ to $C_{12}$ alkenyl or alkynyl group; a preferably $C_3$ to $C_{12}$ cycloalkyl group; or a preferably $C_6$ to $C_{12}$ aryl or arylalkyl group.

$R_{11}$ preferably represents a hydrogen atom or a $C_1$-$C_4$ alkyl group.

It should be noted that, when the nucleophilic substrate comprises an $NH_2$ group in which the two hydrogen atoms are capable of reacting, it is possible, in order to improve the selectivity of the reaction, to block one of them using a protective group. The protective groups commonly used for these purposes are employed, and mention may in particular be made of the groups of BOC (butyloxycarbonyl) or FMOC (trifluoromethyloxycarbonyl) type. Reference may be made to the work by Theodora W. Greene et al, *Protective Groups in Organic Synthesis*, (2nd edition) John Wiley & Sons, Inc., for carrying out the protection of the amino group and also its deprotection.

Hydrazones may be mentioned as other types of nucleophilic substrates. The hydrazones can be represented by the formula below:

$$\begin{array}{c} R_{12} \\ \phantom{R}\diagdown \\ \phantom{RR}C=N-NH-R_{14} \\ \phantom{R}\diagup \\ R_{13} \end{array} \quad (\text{If})$$

in said formula:
   $R_{12}$, $R_{13}$ and $R_{14}$, which may be identical or different, have the meaning given for $R_1$ and $R_2$ in formula (Ia),
   at most one of the groups $R_{12}$ and $R_{13}$ represents a hydrogen atom,
   or else $R_{12}$ and $R_{13}$ may be linked so as to constitute, with the carbon atoms that bear them, a monocyclic or polycyclic, saturated, unsaturated or aromatic, carbocyclic or heterocyclic group having from 3 to 20 atoms.

The hydrazones used preferentially correspond to formula (If) in which $R_{12}$ and $R_{13}$ which may be identical or different, represent a $C_1$ to $C_{15}$, preferably $C_1$ to $C_{10}$ alkyl group, a $C_3$ to $C_8$, preferably $C_5$ or $C_6$, cycloalkyl group, or a $C_6$ to $C_{12}$ aryl or arylalkyl group.

As more specific examples of groups $R_{12}$ and $R_{13}$, mention may be made of $C_1$ to $C_4$ alkyl, phenyl, benzyl or naphthyl groups.

$R_{12}$ and $R_{13}$ may be linked so as to constitute, with the carbon atoms that bear them, a saturated, unsaturated or aromatic, carbocyclic or heterocyclic group having from 3 to 20 atoms, which is monocyclic or polycyclic comprising two or three ortho-condensed rings. In the case of the polycyclic compounds, the number of atoms in each ring varies preferably between 3 and 6. $R_{12}$ and $R_{13}$ preferentially form a ring of cyclohexane or fluorenone type.

In formula (If), $R_{14}$ represents more particularly a hydrogen atom, a preferably $C_1$ to $C_{12}$ alkyl group; a preferably $C_2$ to $C_{12}$ alkenyl or alkynyl group; a preferably $C_3$ to $C_{12}$ cycloalkyl group; or a preferably $C_6$ to $C_{12}$ aryl or arylalkyl group.

$R_{14}$ preferably represents a hydrogen atom or a $C_1$-$C_4$ alkyl group.

Nucleophilic substrates that are entirely suitable for implementing the method of the invention are the heterocyclic derivatives comprising at least one —N—H group.

More specifically, they correspond to general formula (Ig):

$$\begin{array}{c} (R_{15})_n \\ \diagup \\ \bigcirc \\ \diagdown \\ A \end{array} \quad (\text{Ig})$$

in said formula (Ig):
   A symbolizes the residue of a ring forming all or part of a monocyclic or polycyclic, aromatic or nonaromatic heterocyclic system in which one of the carbon atoms is replaced with at least one —NH group,
   $R_{15}$, which may be identical or different, represent substituents on the ring,
   n represents the number of substituents on the ring.

The invention applies in particular to the monocyclic heterocyclic compounds corresponding to formula (Ig) in which A symbolizes a saturated, unsaturated or aromatic heterocycle containing in particular 5 or 6 atoms in the ring that may comprise 1 or 3 heteroatoms, such as nitrogen, sulfur and oxygen atoms, and at least one of which is a nucleophilic atom such as NH.

A may also represent a polycyclic heterocyclic compound defined as consisting of at least 2 aromatic or nonaromatic heterocycles containing at least one heteroatom in each ring and forming with one another ortho-condensed or ortho- and pericondensed systems, or a group consisting of at least one aromatic or nonaromatic carbocycle and at least one aromatic or nonaromatic heterocycle forming with one another ortho-condensed or ortho- and pericondensed systems.

It is also possible to start with a substrate resulting from the linking of a saturated, unsaturated or aromatic heterocycle as mentioned above and a saturated, unsaturated or aromatic carbocycle. The term "carbocycle" is preferably intended to mean a ring of cycloaliphatic or aromatic type having from 3 to 8, preferably 6, carbon atoms.

It should be noted that all or only some of the carbon atoms of the heterocycle may optionally be substituted with groups $R_{15}$.

The number of substituents present on the ring depends on the number of atoms in the ring and on the presence or absence of unsaturations on the ring.

The maximum number of substituents that can be borne by a ring is readily determined by those skilled in the art.

In formula (Ig), n is an integer of less than or equal to 4, preferably equal to 0 or 1.

Examples of substituents are given below, but this list is not limiting in nature.

The group(s) $R_{15}$, which may be identical or different, preferentially represent one of the following groups:
   a $C_1$ to $C_6$, preferably $C_1$ to $C_4$ carbon atoms, linear or branched alkyl group, such as methyl, ethyl, propyl, isopropyl, butyl, isobutyl, sec-butyl or tert-butyl,
   a $C_2$ to $C_6$, preferably $C_2$ to $C_4$, linear or branched alkenyl or alkynyl group, such as vinyl or allyl,
   a $C_1$ to $C_6$, preferably $C_1$ to $C_4$, linear or branched alkoxy or thioether group, such as methoxy, ethoxy, propoxy, isopropoxy or butoxy groups, an alkenyloxy group, preferably an allyloxy group or a phenoxy group,
   a cyclohexyl, phenyl or benzyl group,
   a group or function such as: hydroxyl, thiol, carboxylic, ester, amide, formyl, acyl, aroyl, amide, urea, isocyanate, thioisocyanate, nitrile, azide, nitro, sulfone, sulfonic, halogen, pseudohalogen or trifluoromethyl.

The present invention applies most particularly to the compounds corresponding to formula (Ig) in which the group(s) $R_{15}$ represent more particularly an alkyl or alkoxy group.

More particularly, the optionally substituted residue A represents one of the following rings:
   a monocyclic heterocycle comprising one or more heteroatoms:

-continued

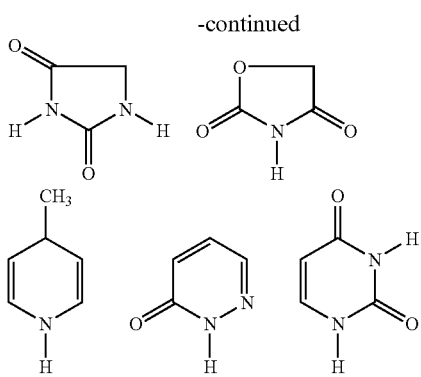

a bicycle comprising a carbocycle and a heterocycle comprising one or more heteroatoms:

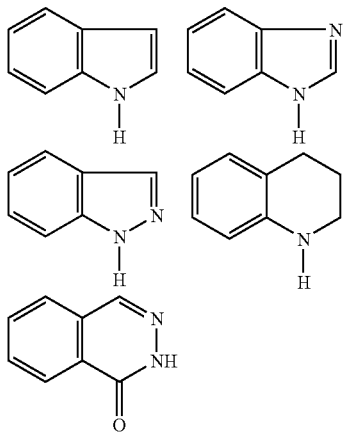

a tricycle comprising at least one carbocycle or a heterocycle comprising one or more heteroatoms:

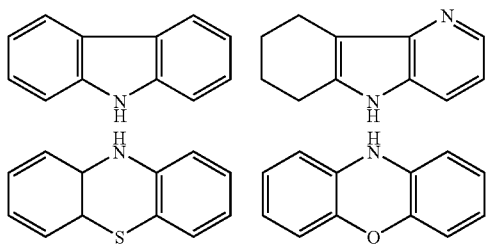

As examples of heterocyclic compounds, use is preferably made of those which correspond to formula (Ig) in which A represents a ring such as: imidazole, pyrazole, triazole, pyrazine, oxadiazole, oxazole, tetrazole, indole, pyrrole, phthalazine, pyridazine or oxazolidine.

The present text gives lists of nucleophilic compounds that are in no way limiting, and any type of nucleophilic compound may be envisioned. In particular, provided that the nucleophilic compound comprises a ring, it is possible for substituents to be present.

For examples of substituents, reference may be made to the meaning given for $R_{15}$ in formula (Ig).

The preferred nucleophiles used in the method of the invention are as follows: diphenylamine, N-methyl-N-phenylamine, benzophenone imine, benzophenone hydrazone, benzophenone oxime.

Aromatic Compound.

In accordance with the method of the invention, the creation of a —C—N— or —C—O— bond is carried out by reacting a nitrogenous or oxygenated nucleophilic compound with a compound comprising an unsaturation in the α-position with respect to a leaving group.

More specifically, it is a compound comprising a leaving group Y symbolized by formula (II):

$$R_0—Y \qquad (II)$$

in said formula (II):

$R_0$ represents a hydrocarbon group comprising from 2 to 20 carbon atoms and has a double bond or a triple bond located in the α-position with respect to a leaving group Y or a monocyclic or polycyclic, aromatic carbocyclic and/or heterocyclic group bearing a leaving group on one ring.

In accordance with the method of the invention, the compound of formula (I) is reacted with a compound of formula (II) in which:

$R_0$ represents an aliphatic hydrocarbon group comprising a double bond or a triple bond in the α-position with respect to the leaving group or an unsaturated cyclic hydrocarbon group in which an unsaturation bears the leaving group, $R_0$ represents a monocyclic or polycyclic, aromatic carbocyclic and/or heterocyclic group, Y represents a leaving group, preferably a halogen atom or a sulfonic ester group of formula —OSO$_2$—R$_e$, in which R$_e$ is a hydrocarbon group.

The compound of formula (II) will subsequently be referred to as "leaving group-bearing compound".

In the formula of the sulfonic ester group, R$_e$ is a hydrocarbon group of any nature. However, given that Y is a leaving group, it is advantageous from an economical point of view for R$_e$ to be simple in nature and to represent more particularly a linear or branched alkyl group having from 1 to 4 carbon atoms, preferably a methyl or ethyl group, but it may also represent, for example, a phenyl or tolyl group or a trifluoromethyl group. Among the groups Y, the preferred group is a triflate group, which corresponds to a group R$_e$ representing a trifluoromethyl group.

A bromine or chlorine atom is preferably chosen as preferred leaving groups.

The compounds of formula (II) targeted most particularly according to the method of the invention may be classified in three groups:

(1) those of aliphatic type bearing a double bond that can be represented by formula (IIa):

in said formula (IIa):

$R_{20}$, $R_{21}$ and $R_{22}$, which may be identical or different, represent a hydrogen atom or a hydrocarbon group having from 1 to 20 carbon atoms, which may be a linear or branched, saturated or unsaturated aliphatic group; a monocyclic or polycyclic, saturated, unsaturated or aromatic, carbocyclic or heterocyclic group; or a chain of aliphatic and/or carbocyclic and/or heterocyclic groups as mentioned above, Y symbolizes the leaving group as defined above, (2) those of aliphatic type bearing a triple bond and that can be represented by formula (IIb):

in said formula (IIb):

$R_{20}$ has the meaning given in formula (IIa),

Y represents a leaving group as defined above, (3) those of aromatic type that are subsequently referred to as "haloaromatic compound" and that can be represented by formula (IIc):

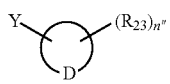

in which:

D symbolizes the residue of a ring forming all or part of a monocyclic or polycyclic, aromatic carbocyclic and/or heterocyclic system, $R_{23}$, which may be identical or different, represent substituents on the ring, Y represents a leaving group as defined above, n" represents the number of substituents on the ring.

The invention applies to the unsaturated compounds corresponding to formulae (IIa) and (IIb) in which $R_{20}$ preferentially represents a linear or branched, acyclic aliphatic group preferably having from 1 to 12 carbon atoms, which is saturated.

The invention does not exclude the presence of another unsaturation on the hydrocarbon chain, such as another triple bond or alternatively one or more double bonds which may or may not be conjugated.

The hydrocarbon chain may be optionally interrupted with a heteroatom (for example, oxygen or sulfur) or with a functional group insofar as the latter does not react, and mention may in particular be made of a group such as especially —CO—.

The hydrocarbon chain may optionally bear one or more substituents insofar as they do not react under the reaction conditions, and mention may in particular be made of a halogen atom, a nitrile group or a trifluoromethyl group.

The linear or branched, saturated or unsaturated, acyclic aliphatic group may optionally bear a cyclic substituent. The term "ring" is intended to mean a monocyclic or polycyclic, saturated, unsaturated or aromatic, carbocyclic or heterocyclic ring.

The acyclic aliphatic group may be connected to the ring via a valency bond, a heteroatom or a functional group such as oxy, carbonyl, carboxy, sulfonyl, etc.

As examples of cyclic substituents, it is possible to envision cycloaliphatic, aromatic or heterocyclic substituents, in particular cycloaliphatic substituents comprising 6 carbon atoms in the ring or benzene substituents, it being possible for these cyclic substituents themselves bear any substituent insofar as they do not hinder the reactions involved in the method of the invention. Mention may in particular be made of alkyl or alkoxy groups having from 1 to 4 carbon atoms.

Among the aliphatic groups bearing a cyclic substituent, aralkyl groups having from 7 to 12 carbon atoms, in particular benzyl or phenylethyl, are more particularly targeted.

In formulae (IIa) and (IIb), $R_{20}$ may also represent a saturated or unsaturated carbocyclic group preferably having 5 or 6 carbon atoms in the ring, preferably cyclohexyl; a saturated or unsaturated heterocyclic group containing in particular 5 or 6 atoms in the ring, including 1 or 2 heteroatoms such as nitrogen, sulfur and oxygen atoms; a monocyclic aromatic carbocyclic group, preferably phenyl, or a condensed or non-condensed polycyclic group, preferably naphthyl.

As regards $R_{21}$ and $R_{22}$, they preferentially represent a hydrogen atom or an alkyl group having from 1 to 12 carbon atoms, a phenyl group or an aralkyl group having from 7 to 12 carbon atoms, preferably a benzyl group.

In formulae (IIa) and/or (IIb), $R_{20}$, $R_{21}$ and $R_{22}$ represent more particularly a hydrogen atom, or $R_{20}$ represents a phenyl group and $R_{21}$ and $R_{22}$ represent a hydrogen atom.

It should also be noted that the groups $R_{20}$ and $R_{21}$ may also represent a functional group insofar as the latter does not interfere in the coupling reaction. As examples, mention may be made of functions such as amido, ester, ether or cyano.

As examples of compounds corresponding to formulae (IIa) and (IIb), mention may in particular be made of vinyl chloride, vinyl bromide, β-bromo- or β-chlorostyrene, bromoalkyne or iodoalkyne.

The invention applies in particular to the haloaromatic compounds corresponding to formula (IIc) in which D is the residue of a cyclic compound preferably having at least 4 atoms in the ring, preferably 5 or 6, which is optionally substituted, and which represents at least one of the following rings:

a monocyclic or polycyclic aromatic carbocycle, i.e. a compound consisting of at least 2 aromatic carbocycles which form with one another ortho-condensed or ortho- and pericondensed systems, or a compound consisting of at least 2 carbocycles, of which only one is aromatic and which form with one another ortho-condensed or ortho- and pericondensed systems, a monocyclic aromatic heterocycle containing at least one of the heteroatoms P, O, N and S, or a polycyclic aromatic heterocycle, i.e. a compound consisting of at least 2 heterocycles containing at least one heteroatom in each ring, in which at least one of the two rings is aromatic, and forming with one another ortho-condensed or ortho- and pericondensed systems, or a compound consisting of at least one carbocycle and at least one heterocycle, at least one of the rings of which is aromatic, and which form with one another ortho-condensed or ortho- and pericondensed systems.

More particularly, the optionally substituted residue D preferentially represents the residue of an aromatic carbocycle such as benzene, of an aromatic bicycle comprising two aromatic carbocycles, such as naphthalene, or a partially aromatic bicycle comprising two carbocycles, one of which is aromatic, such as tetrahydro-1,2,3,4-naphthalene.

The invention also envisions the fact that D may represent the residue of a heterocycle insofar as it is more electrophilic than the compound corresponding to formula (Ig).

As particular examples, mention may be made of an aromatic heterocycle such as furan or pyridine; an aromatic bicycle comprising an aromatic carbocycle and an aromatic heterocycle, such as benzofuran or benzopyridine, a partially aromatic bicycle comprising an aromatic carbocycle and a heterocycle, such as methylenedioxybenzene; an aromatic bicycle comprising two aromatic heterocycles, such as 1,8-naphthylpyridine; or a partially aromatic bicycle comprising a carbocycle and an aromatic heterocycle, such as tetrahydro-5,6,7,8-quinoline.

In the method of the invention, a haloaromatic compound of formula (IIc) in which D represents an aromatic ring, preferably a benzene or naphthalene ring, is preferentially used.

The aromatic compound of formula (IIc) may bear one or more substituents.

In the present text, the term "more" is generally intended to mean less than 4 substituents $R_{23}$ on an aromatic ring.

For examples of substituents, reference may be made to the meaning given for $R_{15}$ in formula (Ig).

$R_{23}$ also represents a saturated, unsaturated or aromatic heterocycle comprising 5 or 6 atoms and comprising, as heteroatom, sulfur, oxygen or nitrogen. Mention may in particular be made of pyrazolyl or imidazolyl groups.

In formula (IIc), n" is a number of less than or equal to 4, preferably equal to 1 or 2.

As examples of compounds corresponding to formula (IIc), mention may in particular be made of p-chlorotoluene, p-bromoanisole or p-bromotrifluorobenzene.

The amount of the leaving group-bearing unsaturated compound of formula (II), preferably of formula (IIa) or (IIb) or (IIc), used is generally expressed relative to the amount of the nucleophilic compound in the region of the stoichiometry. Thus, the ratio of the number of moles of the leaving group-bearing unsaturated compound to the number of moles of the nucleophilic compound ranges most commonly between 0.9 and 1.5, preferably between 1 and 1.2.

Catalyst.

In accordance with the method of the invention, the nucleophilic compound preferably corresponding to formulae (Ia) to (Ig) is reacted with a leaving group-bearing compound corresponding to formula (II), preferably of formula (IIa) or (IIb) or (IIc), in the presence of an effective amount of a palladium-based catalyst and a ligand as defined according to the invention.

The catalysts used in the method of the invention are known products.

The palladium may be introduced in the form of a finely divided metal or in the form of an inorganic derivative such as an oxide or a hydroxide. It is possible to use a mineral salt, preferably nitrate, sulfate, oxysulfate, halide, oxyhalide or carbonate, or an organic derivative, preferably cyamide, oxalate, acetylacetonate; alkoxide, and even more preferentially methoxide or ethoxide; carboxylate, and even more preferentially acetate. It is also possible to use complexes, in particular chlorinated or cyanated complexes, of Pd metals and/or of alkali metals, preferably sodium or potassium, or of ammonium.

By way of examples of compounds that can be used for preparing the catalysts of the invention, mention may in particular be made of palladium (II) bromide, palladium (II) chloride, palladium (II) iodide, palladium (II) cyamide, palladium (II) nitrate hydrate, palladium (II) oxide, palladium (II) sulfate dihydrate, palladium (II) acetate, palladium (II) propionate, palladium (II) butyrate, palladium (II) benzoate, palladium (II) acetylacetonate, ammonium tetrachloropalladate (II), potassium hexachloropalladate (IV), palladium (II) tetramine nitrate, palladium (II) dichlorobis(acetonitrile), palladium (II) dichlorobis(benzonitrile), palladium (II) dichloro(1,5-cyclooctadiene), palladium (II) dichlorodiamine, palladium (0) tetrakistriphenylphosphine, palladium (II) acetate and trisbenzylidene acetone palladium (0).

The compound in solution can be deposited onto a support.

A metallic form can also be deposited onto a support.

The support is chosen such that it is inert under the reaction conditions.

As examples of supports, use may be made of a mineral or organic support such as, in particular, charcoal, activated charcoal, carbon black, silica, alumina, preferably β-alumina, titanium oxide, preferably anatase, zirconium oxide, barium sulfate, or natural or synthetic zeolites, for example β or Y zeolites.

The deposition may be carried out in a conventional manner, for example by adsorption onto the support or else according to a sol/gel process, especially in the case of silica, of titanium oxide or of zirconium oxide.

Generally, the metal is deposited at a rate of 0.5% to 10%, preferably of 1% to 5% of the weight of the catalyst.

Among the abovementioned catalysts, the preferred catalyst is palladium chloride, palladium acetate or palladium-on-charcoal.

The catalyst may be used in the form of a powder, of pellets or else of granules.

The amount of compound introducing the Pd element, that is used, expressed by the molar ratio of the number of moles of said compound to the number of moles of compound of formula (II), generally ranges between 0.005 and 1, preferably between 0.01 and 0.1.

According to a preferred variant of the invention, which consists in introducing a suspension of metal hydroxide or ammonium hydroxide prepared by wet milling, it is possible to decrease the amount of palladium used.

Thus, the molar ratio of the number of moles of said compound to the number of moles of compound of formula (II) advantageously ranges between 0.005 and 0.5, preferably between 0.005 and 0.01.

Ligand:

A ligand, preferably of organophosphate type, is involved in the method of the invention, which ligand can be chosen preferably from phosphines or phosphites or phosphonites which complex the metal element.

This complex is generally produced in situ between the compound introducing the Pd metal element and the ligand present. However, said complex can also be prepared extemporaneously and introduced into the reaction medium. An additional amount of free ligand may or may not then be added.

The choice of the ligand has an influence on the selectivity of the reaction.

A first class of ligands are phosphines.

Use is preferentially made of aliphatic, cycloaliphatic, arylaliphatic or aromatic phosphines or of mixed, aliphatic and/or cycloaliphatic and/or arylaliphatic and/or aromatic phosphines.

These phosphines are in particular those which correspond to general formula (IIIa):

(IIIa)

in said formula:
q is equal to 0 or 1,
the groups $R_a$, $R_b$, $R_c$ and $R_d$, which may be identical or different, represent:
an alkyl group having from 1 to 12 carbon atoms,
a cycloalkyl group having 5 or 6 carbon atoms, a cycloalkyl group having 5 or 6 carbon atoms, which is substituted with one or more alkyl groups having 1 to 4 carbon atoms, or alkoxy groups having 1 or 4 carbon atoms, a phenylalkyl group in which the aliphatic portion contains from 1 to 6 carbon atoms, a phenyl or biphenyl group, a phenyl or biphenyl group substituted with one or more alkyl groups having from 1 to 4 carbon atoms or alkoxy groups having from 1 to 4 carbon atoms, one or more halogen atoms, or a trifluoromethyl group, the group $R_e$ represents:

a valency bond or a saturated or unsaturated, linear or branched divalent hydrocarbon group having from 1 to 6 carbon atoms, an aromatic group of formula:

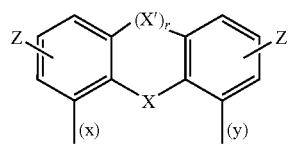

in which:

Z represents a hydrogen atom, an alkyl group having from 1 to 10 carbon atoms, a halogen atom or a trifluoromethyl group, X is an oxygen or sulfur atom or a linear or branched alkylene group having from 1 to 3 carbon atoms, if r is equal to 1, X' represents a valency bond, an oxygen, sulfur or silicon atom or a linear or branched alkylene group having from 1 to 3 carbon atoms, if r is equal to 0, the two rings are not linked, (x) and (y) pinpoint respectively the two bonds established between the group $R_e$ symbolized by formula (IV) and the phosphorus atoms, an aromatic group of formula:

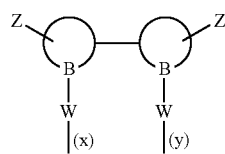

in which:

Z has the meaning given above,

B represents the residue of a benzene or naphthalene ring,

W represents a valency bond or a linear or branched alkylene group having from 1 to 3 carbon atoms, (x) and (y) pinpoint respectively the two bonds established between the group $R_e$ symbolized by formula (V) and the phosphorus atoms, a ferrocene group of formula:

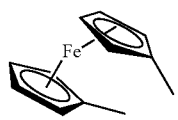

Other phosphines suitable for implementing the method of the invention correspond to general formula (IIIb):

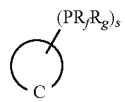

in which:

C represents the residue of a pentane or cyclohexane ring, $R_f$ and $R_g$, which may be identical or different, have the meaning given for $R_a$ or $R_b$, in formula (IIIa), s is a number equal to 1 to 6, preferably equal to 4.

In formula (IIIb), C is preferentially the residue of a cyclohexane and $R_f$ and $R_g$ represent a phenyl group, the number s being equal to 4.

A ligand of phosphite or phosphonite type may also be used, and in particular those corresponding to formula (IIIc).

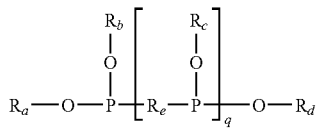

in said formula, the groups $R_a$, $R_b$, $R_c$, $R_d$ and $R_e$, and the symbol q have the meaning given for formula (IIIa).

By way of examples of such phosphines, mention may be made, in a nonlimiting manner, of: tricyclohexylphosphine, trimethylphosphine, triethylphosphine, tri-n-butylphosphine, triisobutylphosphine, tri-tert-butylphosphine, tribenzylphosphine, dicyclohexylphenylphosphine, 2-dicyclohexylphosphino-2-methylbiphenyl, triphenylphosphine, dimethylphenylphosphine, diethylphenylphosphine, di-tert-butylphenylphosphine, tri(p-tolyl)phosphine, isopropyldiphenylphosphine, tris(pentafluorophenyl)phosphine, tri(o-tolyl)phosphine, bisdiphenylphosphinomethane, bisdiphenylphosphinoethane, bisdiphenylphosphinopropane, bisdiphenylphosphinobutane, bisdiphenylphosphinopentane, bisdiphenylphosphinoferrocene, 2,2'-bis(diphenylphosphino)-1,1'-binaphthyl (BINAP), bis-[(2-diphenylphosphino)phenyl]ether (DPEPHOS), 4,5-bis(diphenylphosphino)-9,9-dimethylxanthene (XANTPHOS), tetrakis-(2,4-di-tert-butylphenyl)-4,4'-diphenylenebisphosphonite.

The amount of ligand, expressed by the ratio of the number of moles of ligand (expressed with respect to the phosphorus atom) to the number of moles of catalyst (expressed with respect to the metal element), ranges between 1 and 5, preferably between 2 and 3.

Base

A base, the function of which is to trap the leaving group, is also involved in the method of the invention.

In accordance with the method of the invention, use is made of an ammonium hydroxide or of a monovalent metal hydroxide or a bivalent metal hydroxide, preferably an alkali and/or alkaline earth metal hydroxide.

As more specific examples of bases to be used, mention may be made of an alkali metal hydroxide, such as sodium hydroxide, potassium hydroxide or cesium hydroxide, and an alkaline earth metal hydroxide, such as magnesium hydroxide, calcium hydroxide or barium hydroxide; a hydroxide of a metal of group IIB, such as zinc.

Among the bases, sodium hydroxide or potassium hydroxide is preferentially chosen.

The base may be in a solid form or in an aqueous solution that is preferably very concentrated, for example from 10 to 5 mol/liter, preferably in the region of 12 mol/liter.

The amount of base used is such that the ratio of the number of moles of base to the number of moles of the leaving group-bearing aromatic compound preferentially ranges between 1 and 1.4.

Alcohol-type Solvent.

The alcohol-type-solvent that is involved in the method of the invention can be symbolized by the formula below:

$$R_h\text{---OH} \quad (VI)$$

in said formula (VI):

$R_h$ represents an optionally substituted hydrocarbon group having from 1 to 24 carbon atoms, which may be a linear or branched, saturated or unsaturated acyclic aliphatic group; a monocyclic or polycyclic, saturated or unsaturated cycloaliphatic group; or a linear or branched, saturated or unsaturated aliphatic group bearing a cyclic substituent.

The solvent chosen preferentially corresponds to formula (VI) in which $R_h$ represents a linear or branched, saturated or unsaturated acylic aliphatic group.

$R_h$ preferentially represents a linear or branched acyclic aliphatic group preferably having from 1 to 12 carbon atoms, which is saturated.

The invention does not exclude the presence of an unsaturation on the hydrocarbon chain, such as a double or triple bond or alternatively one or more double bonds which may or may not be conjugated.

The hydrocarbon chain may be optionally interrupted with a heteroatom (for example, oxygen or sulfur) or with a functional group insofar as the latter does not react, and mention may in particular be made of a group such as especially —CO—.

The hydrocarbon chain may optionally bear one of the following substituents: —$OR_i$, —$NR_iR_i$, in these formulae, the groups $R_i$, which may be identical or different, represent hydrogen or a linear or branched alkyl group having from 1 to 4 carbon atoms, preferably a methyl or ethyl group or a phenyl group.

The linear or branched, saturated or unsaturated acyclic aliphatic group may optionally bear a cyclic substituent. The term "ring" is intended to mean a saturated, unsaturated or aromatic, carbocyclic or heterocyclic ring.

The acyclic aliphatic group may be connected to the ring via a valency bond, a heteroatom or a functional group such as, oxy, carbonyl, carboxy, sulfonyl, etc.

The linear or branched, saturated or unsaturated acyclic aliphatic residue may optionally bear a cyclic substituent. The term "ring" is intended to mean a saturated, unsaturated or aromatic, carbocyclic or heterocyclic ring.

The acyclic aliphatic residue may be connected to the ring via a valency bond or via an atom or a functional group, for example —O—.

As examples of cyclic substituents, it is possible to envision cycloaliphatic, aromatic or heterocyclic substituents, in particular cycloaliphatic substituents comprising 6 carbon atoms in the ring or benzene substituents or heterocyclic substituents containing 5 or 6 atoms in the ring, including one or two heteroatoms such as nitrogen (not substituted with a hydrogen atom), sulfur and oxygen atoms. It is possible for there to be a substituent insofar as they do not interfere in the coupling reaction. Mention may in particular be made of alkyl or alkoxy groups having from 1 to 4 carbon atoms.

In general formula (VI), $R_h$ may also represent a carbocyclic group which is saturated or which comprises 1 or 2 unsaturations in the ring, generally having from 3 to 7 carbon atoms, preferably 6 carbon atoms in the ring; it being possible for said ring to be substituted with 1 to 5 groups $R_5$, preferably 1 to 3, $R_5$ having the meanings stated above.

As preferred examples of groups $R_h$, mention may be made of cyclohexyl or cyclohexenyl groups optionally substituted with linear or branched alkyl groups having from 1 to 4 carbon atoms.

The solvents used may be of the mono- or polyalcohol, ether alcohol or amino alcohol type, or mixtures thereof.

In the class of alcohols, preference is given to primary or tertiary alcohols and secondary alcohols provided that they are hindered, i.e. the two carbon atoms in the α-position are substituted.

As examples of alcohols, mention may be made of lower aliphatic alcohols having from 1 to 5 carbon atoms, for instance methanol, ethanol, trifluoroethanol, propanol, isopropyl alcohol, butanol, isobutyl alcohol, sec-butyl alcohol, tert-butanol, pentanol, isopentyl alcohol, sec-pentyl alcohol and tert-pentyl alcohol, ethylene glycol monoethyl ether, and also higher aliphatic alcohols having at least 6 and up to approximately 20 carbon atoms, for instance hexanol, heptanol, isoheptyl alcohol, octanol, isooctyl alcohol, 2-ethylhexanol, sec-octyl alcohol, tert-octyl alcohol, nonanol, isononyl alcohol, decanol, dodecanol, tetradecanol, octadecanol, hexadecanol, oleyl alcohol, eicosyl alcohol, and diethylene glycol monoethyl ether. Cycloaliphatic alcohols having from 3 to approximately 20 carbon atoms can be used, for instance cyclopropanol, cyclobutanol, cyclopentanol, cyclohexanol, cycloheptanol, cyclooctanol, cyclododecanol, tripropylcyclohexanol, methylcyclohexanol and methylcycloheptanol, or else an aliphatic alcohol bearing an aromatic group having from 7 to approximately 20 carbon atoms, for instance benzyl alcohol, phenethyl alcohol, phenylpropyl alcohol, phenyloctadecyl alcohol and naphthyldecyl alcohol, or an aliphatic alcohol bearing a heterocyclic group, for example furfurol.

It is also possible to use polyols (in particular polyoxyethylene glycols), for instance ethylene glycol, benzyl glycol, diethylene glycol, triethylene glycol, propylene glycol or glycerol.

Among the abovementioned alcohols, primary or tertiary alcohols having from 1 to 4 carbon atoms are preferably used in the method of the invention.

Mention may also be made, as an example of an amino alcohol-type solvent, of N,N-dimethylethanolamine; and, as examples of ether alcohol-type solvents, of methoxyethanol or 1-methoxypropan-2-ol (Dowanol®).

The preferred solvents are tert-butanol, tert-amyl alcohol, methoxyethanol or ethylene glycol.

The amount of alcohol-type solvent used is determined such that the concentration of the leaving group-bearing compound in the organic solvent is preferably between 0.5 and 2 mol/liter, preferably in the region of 1 mol/liter.

Cosolvent.

According to a variant of the method of the invention, the alcohol-type solvent can be combined with another solvent, preferably of apolar aprotic type.

It is therefore possible for there to be a cosolvent, and mention may more particularly be made of aliphatic, cycloaliphatic or aromatic hydrocarbons.

By way of examples of aliphatic hydrocarbons, mention may more particularly be made of paraffins, for instance especially hexane, cyclohexane, methyl-cyclohexane, or petroleum cuts of petroleum ether type. Mention may more particularly be made of aromatic hydrocarbons such as, in particular, benzene, toluene, xylenes, cumene, mesitylene, or petroleum cuts consisting of a mixture of alkylbenzenes, in particular cuts of Solvesso type.

It should be noted that the amount of cosolvent used may represent from 1 to 50% of the volume of the alcohol-type solvent, preferably from 10 to 20%.

As regards the temperature of the reaction between the nucleophilic compound and the leaving group-bearing unsaturated compound, it is advantageously chosen such that the reactants are in the liquid state.

The coupling reaction takes place at a temperature which is situated between 50° C. and 200° C., preferably between 80° C. and 150° C., and even more preferentially between 90° C. and 110° C.

The coupling reaction is generally carried out under atmospheric pressure, but higher pressures that can reach, for example, 10 bar, may also be used.

From a practical point of view, the reaction is simple to carry out.

A first method of using the reactants consists in loading the leaving group-bearing compound of formula (II), the base, the alcohol-type solvent and, optionally, the cosolvent.

Another method of preparation, which is preferred, is to prepare the suspension of metal hydroxide or ammonium hydroxide in the alcohol by wet milling.

The operation can be carried out in any type of mill resistant to corrosion by the base (for example made of stainless steel), and more particularly in a wet ball mill.

It is most commonly carried out at ambient temperature (generally between 15 and 25° C.

A preferred order consists in loading the alcoholic solvent, preferably the tert-amyl alcohol or the tert-butanol, into the mill, and then introducing the base, preferably sodium hydroxide, in solid form (already milled or in the form of pellets). Milling is carried out until a homogeneous suspension is obtained.

The suspension recovered is used during the coupling reaction.

Generally, the leaving group-bearing compound of formula (II) and, optionally, the cosolvent are introduced therein.

Next, whatever the method of preparation, the catalyst is added preformed or not preformed, which means that the Pd metal element can be introduced either already in the form of a complex comprising one of the ligands mentioned above, or else the Pd metal element and the ligand are introduced into the medium separately.

The metal complex can be prepared, at the beginning of the reaction, from the ligand and the compound introducing the Pd metal element.

The catalytic complex can be obtained, for example, by heating the compound introducing the Pd element and the ligand, to between 20° C. and 60° C., preferentially to 20° C., in the solvent(s) used to carry out the reaction.

After introduction of the catalyst, the reaction medium is brought to the selected reaction temperature.

The nucleophilic compound preferably corresponding to one of the formulae (Ia) to (Ig) is added.

Said compound can be added in solid or molten form or in solution in the abovementioned solvent(s), either in one batch, or fractionwise or continuously.

The progression of the reaction is verified by following the disappearance of the leaving group-bearing compound.

Another embodiment of the method of the invention consists in loading the suspension of base, preferably sodium hydroxide, in the alcoholic solvent prepared by wet milling, and adding the leaving group-bearing compound and the nucleophilic compound. Next, the palladium catalyst is added and the reaction medium is brought to the selected reaction temperature. It is possible to add a surplus of alcoholic solvent or a cosolvent.

At the end of the reaction, a product of the type $R\text{-}Nu\text{-}R_0$ is obtained, R representing the residue of the nucleophilic compound, and more particularly an arylated product comprising the residue of the nucleophilic compound and the residue of the electrophilic compound, which preferentially corresponds to formula (VII) below:

(VII)

in said formula (VII), D, R, $R_{23}$ and n″ have the meaning given above and Nu represents an oxygen or nitrogen atom.

The compound obtained is recovered according to the conventional techniques used.

The desired product can, for example, be extracted in an organic solvent, for example a hydrocarbon, preferably xylene.

Generally, the organic phase is concentrated and the product is precipitated by adding a cosolvent, in particular methanol, ethanol or isopropanol.

The precipitated product is separated according to the conventional techniques of solid-liquid separation, in particular by filtration.

Examples of implementation of the invention are given hereinafter. These examples are given by way of indication and are not limiting in nature.

In the examples, the conversion rate (CR) corresponds to the ratio of the number of moles of substrate converted to the number of moles of substrate initially used.

The yield (RR) corresponds to the ratio of the number of moles of product formed to the number of moles of substrate initially used.

The selectivity (RT) corresponds to the ratio of the number of moles of product formed to the number of moles of substrate converted.

EXAMPLE 1

448 mg of milled sodium hydroxide (1.4 eq; 11.2 mmol), 1.368 g of 4-bromotoluene (1 eq; 8 mmol) and 1.57 g of benzophenone hydrazone (1 eq; 8 mmol) in 7 ml of 2-methoxyethanol are loaded into a 20 ml reactor surmounted by a condenser, a magnetic stirrer and a temperature sensor, and placed under an inert atmosphere.

8.1 mg of palladium acetate and 26.1 mg of 2-dicyclohexylphosphino-2-methylbiphenyl in 7 ml of degassed xylene are loaded into a 5 ml Schlenk tube equipped with a magnetic stirrer and placed under an inert atmosphere.

After stirring for twenty minutes, the catalyst (0.005 eq; 0.5 mol %; 1 ml) is transferred into the reactor.

After stirring at 105° C. for three hours, the conversion of the 4-bromotoluene is complete (CR=100%), and a benzophenone N-tolylhydrazone yield (RT) of 91% is determined by gas chromatography in the presence of an internal standard (hexacosane).

EXAMPLE 2

448 mg of milled sodium hydroxide (1.4 eq; 11.2 mmol), 1.368 g of 4-bromotoluene (1 eq; 8 mmol) and 1.57 g of benzophenone hydrazone (1 eq; 8 mmol) in 7 ml of ethylene glycol are loaded into a 20 ml reactor surmounted by a condenser, a magnetic stirrer and a temperature sensor, and placed under an inert atmosphere.

8.1 mg of palladium acetate and 26.1 mg of 2-dicyclohexylphosphino-2-methylbiphenyl in 7 ml of degassed xylene are loaded into a 5 ml Schlenk tube equipped with a magnetic stirrer and placed under an inert atmosphere.

After stirring for twenty minutes, the catalyst (0.005 eq; 0.5 mol %; 1 ml) is transferred into the reactor.

After stirring at 105° C. for twenty hours, the conversion of the 4-bromotoluene is complete (CR=100%) and the benzophenone N-tolylhydrazone yield RT of 35% is measured by gas chromatography in the presence of an internal standard (hexacosane).

EXAMPLE 3

448 mg of milled sodium hydroxide (1.4 eq; 11.2 mmol), 1.368 g of 4-bromotoluene (1 eq; 8 mmol) and 1.57 g of benzophenone hydrazone (1 eq; 8 mmol) in 7 ml of N,N-dimethylethanolamine are loaded into a 20 ml reactor surmounted by a condenser, a magnetic stirrer and a temperature sensor, and placed under an inert atmosphere.

8.1 mg of palladium acetate and 26.1 mg of 2-dicyclohexylphosphino-2-methylbiphenyl in 7 ml of degassed xylene are loaded into a 5 ml Schlenk tube equipped with a magnetic stirrer and placed under an inert atmosphere.

After stirring for twenty minutes, the catalyst (0.005 eq; 0.5 mol %; 1 ml) is transferred into the reactor.

After stirring at 105° C. for twenty hours, the conversion of the 4-bromotoluene is complete and a benzophenone N-tolylhydrazone yield of 27% is measured by gas chromatography in the presence of an internal standard (hexacosane).

EXAMPLE 4

11.2 g of milled sodium hydroxide (1.4 eq; 0.28 mol) and 34.2 g of 4-bromotoluene (1 eq; 0.2 mol) in 200 ml of degassed t-butanol are loaded into a 500 ml reactor surmounted by a condenser, a mechanical stirrer and a temperature sensor, and placed under an inert atmosphere.

44.9 mg of palladium acetate (0.1 mol %; 0.0002 mol) and 145.6 mg of 2-dicyclohexylphosphino-2-methylbiphenyl (0.0004 mol) in 20 ml of degassed t-butanol are loaded into a 100 ml Schlenk tube equipped with a magnetic stirrer and placed under an inert atmosphere.

After stirring for twenty minutes, the catalyst thus prepared is transferred into the reactor.

The solution is brought to 84° C. and the solid benzophenone hydrazone (6.5 g×6; 1 eq; 0.2 mol) is regularly added portionwise for two hours.

After stirring for six hours, the conversion of the 4-bromotoluene is complete (CR=100%) and a benzophenone N-tolylhydrazone yield RR of 87% is measured by gas chromatography in the presence of an internal standard (hexacosane).

EXAMPLE 5

33.6 g of milled sodium hydroxide (1.4 eq; 0.84 mol) and 102.62 g of 4-bromotoluene (1 eq; 0.6 mol) in 240 ml of degassed t-butanol are loaded into a 500 ml reactor surmounted by a condenser, a mechanical stirrer and a temperature sensor, and placed under an inert atmosphere.

135 mg of palladium acetate (0.1 mol %; 0.0006 mol) and 437 mg of 2-dicyclohexylphosphino-2-methylbiphenyl (0.0012 mol) in 30 ml of degassed t-butanol are loaded into a 100 ml Schlenk tube equipped with a magnetic stirrer and placed under an inert atmosphere.

After stirring for twenty minutes, the catalyst thus prepared is transferred into the reactor.

The solution is brought to 84° C. and the solid benzophenone hydrazone (29.4 g×4; 1 eq; 0.6 mol) is regularly added portionwise for two hours.

After stirring for twelve hours, the mixture is hydrolyzed with 100 ml of demineralized water and 150 ml of xylene are added.

The phases are separated.

By cooling (3° C.), the benzophenone N-tolylhydrazone crystallizes from the organic phase.

After filtration and washing with ethanol, the benzophenone N-tolylhydrazone is obtained in the form of pale yellow crystals, with an isolated yield of 87.4% (confirmed by an analytical yield of 89% and an NMR purity of 98%).

EXAMPLE 6

11.2 g of sodium hydroxide in the form of microbeads (1.4 eq; 0.28 mol; diameter 0.7 mm) and 34.2 g of 4-bromotoluene (1 eq; 0.2 mol) in 200 ml of degassed t-butanol are loaded into a 500 ml reactor surmounted by a condenser, a mechanical stirrer and a temperature sensor, and placed under an inert atmosphere.

44.9 mg of palladium acetate (0.1 mol %; 0.0002 mol) and 145.6 mg of 2-dicyclohexylphosphino-2-methylbiphenyl (0.0004 mol) in 15 ml of degassed xylene are loaded into a 100 ml Schlenk tube equipped with a magnetic stirrer and placed under an inert atmosphere.

After stirring for twenty minutes, the catalyst thus prepared is subsequently transferred into the reactor.

The solution is brought to 84° C. and the solid benzophenone hydrazone (13.1 g×3; 1 eq; 0.2 mol) is regularly added portionwise for two hours.

After stirring for twenty hours, the benzophenone N-tolylhydrazone is obtained with an analytical yield of 92% (internal reference: hexacosane).

EXAMPLE 7

588.8 g of benzophenone hydrazone in 800 ml of degassed tert-butanol are loaded into a 2 l reactor surmounted by a condenser, a mechanical stirrer and a temperature sensor, and placed under an inert atmosphere.

This reactor is assembled in cascade with a 6 l reactor surmounted by a condenser, a mechanical stirrer and a temperature sensor, and placed under an inert atmosphere, into which 168 g of sodium hydroxide in the form of microbeads (1.4 eq; 4.2 mol; diameter 0.7 mm) and 513 g of 4-bromotoluene (1 eq; 3 mol) in 2 l of degassed t-butanol are loaded.

673.5 mg of palladium acetate (0.1 mol %; 0.003 mol) and 2.184 g of 2-dicyclohexylphosphino-2-methylbiphenyl (0.006 mol) in 200 ml of degassed toluene are loaded into a 100 ml Schlenk tube equipped with a magnetic stirrer and placed under an inert atmosphere.

After stirring for twenty minutes, the catalyst thus prepared is transferred into the 6 l reactor.

The reaction mixture is brought to 84° C.

The benzophenone hydrazone in solution is run into the 6 l reactor in approximately 1 h 30 min.

After stirring for twenty hours, the mixture is hydrolyzed with 2 l of demineralized water and 2 l of xylene are added.

The organic phase is separated and concentrated under reduced pressure (approximately 8 mm of mercury).

Crystallization from ethanol at 3° C. makes it possible to obtain the benzophenone N-tolylhydrazone in the form of pale yellow crystals, with an isolated yield of 90% (NMR purity of 97%).

EXAMPLE 8

An aqueous solution of sodium hydroxide (11.2 g; 1.4 eq; 0.28 mmol in 20 ml of demineralized water), the 4-bromotoluene (34.2 g; 1 eq; 0.2 mol) and the benzophenone hydrazone (39.4 g; 1 eq; 0.2 mol) in 200 ml of degassed t-butanol are loaded into a 500 ml reactor surmounted by a condenser, a mechanical stirrer and a temperature sensor, and placed under an inert atmosphere.

44.9 mg of palladium acetate (0.1 mol %; 0.0002 mol) and 145.6 mg of 2-dicyclohexylphosphino-2-methylbiphenyl (0.0004 mol) in 20 ml of degassed toluene are loaded into a 100 ml Schlenk tube equipped with a magnetic stirrer and placed under an inert atmosphere.

After stirring for twenty minutes, the catalyst thus prepared is transferred into the reactor.

After stirring for twenty-two hours at 84° C., the benzophenone N-tolylhydrazone is obtained with an analytical yield of 45% (internal reference: hexacosane).

EXAMPLE 9

11.2 g of sodium hydroxide (1.4 eq; 0.28 mol), 34.2 g of 4-bromotoluene (1 eq; 0.2 mol) and 39.4 g of benzophenone hydrazone (1 eq; 0.2 mol) in 190 ml of degassed tert-amyl alcohol are loaded into a 500 ml reactor surmounted by a condenser, a mechanical stirrer and a temperature sensor, and placed under an inert atmosphere.

44.9 mg of palladium acetate (0.1 mol %; 0.0002 mol) and 145.6 mg of 2-dicyclohexylphosphino-2-methylbiphenyl (0.0004 mol) in 20 ml of degassed tert-amyl alcohol are loaded into a 100 ml Schlenk tube equipped with a magnetic stirrer and placed under an inert atmosphere.

After stirring for twenty minutes, the catalyst thus prepared is transferred into the reactor.

After stirring at 103° C. for one hour, the reaction mixture is hydrolyzed with 100 ml of water and 100 ml of xylene are added.

The organic phase is separated and concentrated under reduced pressure (approximately 8 mm of mercury).

Crystallization from ethanol makes it possible to isolate the benzophenone N-tolylhydrazone in the form of pale yellow crystals, with a yield of 92% (NMR purity of 98%).

EXAMPLE 10

11.2 g of sodium hydroxide (1.4 eq; 0.28 mol), 34.2 g of 4-bromotoluene (1 eq; 0.2 mol) and 39.4 g of benzophenone hydrazone (1 eq; 0.2 mol) in 190 ml of degassed tert-amyl alcohol are loaded into a 500 ml reactor surmounted by a condenser, a mechanical stirrer and a temperature sensor, and placed under an inert atmosphere.

22.4 mg of palladium acetate (0.05 mol %; 0.0001 mol) and 72.8 mg of 2-dicyclohexylphosphino-2-methylbiphenyl (0.0002 mol) in 20 ml of degassed tert-amyl alcohol are loaded into 100 ml Schlenk tube equipped with a magnetic stirrer and placed under an inert atmosphere.

After stirring for twenty minutes, the catalyst thus prepared is transferred into the reactor.

After stirring at 103° C. for six hours, the benzophenone N-tolylhydrazone is obtained with an analytical yield of 89% (internal standard: hexacosane).

EXAMPLE 11

11.2 g of sodium hydroxide (1.4 eq; 0.28 mmol), 34.2 g of 4-bromotoluene (1 eq; 0.2 mol) and 39.4 g of benzophenone hydrazone (1 eq; 0.2 mol) in 190 ml of degassed tert-amyl alcohol are loaded into a 500 ml reactor surmounted by a condenser, a mechanical stirrer and a temperature sensor, and placed under an inert atmosphere.

4.48 mg of palladium acetate (0.001 mol %; 0.00002 mol) and 14.56 mg of 2-dicyclohexylphosphino-2-methylbiphenyl 0.00004 mol) in 20 ml of degassed tert-amyl alcohol are loaded into a 100 ml Schlenk tube equipped with a magnetic stirrer and placed under an inert atmosphere.

After stirring for twenty minutes, the catalyst thus prepared is transferred into the reactor.

After stirring at 103° C. for 48 hours, the benzophenone N-tolylhydrazone is obtained with an analytical yield of 48% (internal standard: hexacosane).

EXAMPLE 12

11.2 g of sodium hydroxide (1.4 eq; 0.28 mol), 38.29 g of 4-bromo-chlorobenzene (1 eq; 0.2 mol) and 39.4 g of benzophenone hydrazone (1 eq; 0.2 mol) in 180 ml of degassed tert-amyl alcohol are loaded into a 500 ml reactor surmounted by a condenser, a mechanical stirrer and a temperature sensor, and placed under an inert atmosphere.

44.9 mg of palladium acetate (0.1 mol %; 0.0002 mol) and 145.6 mg of 2-dicyclohexylphosphino-2-methylbiphenyl (0.0004 mol) in 20 ml of degassed xylene are loaded into a 100 ml Schlenk tube equipped with a magnetic stirrer and placed under an inert atmosphere.

After stirring for twenty minutes, the catalyst thus prepared is transferred into the reactor.

After stirring at 103° C. for one hour, the reaction mixture is hydrolyzed with 100 ml of water and 100 ml of xylene are added.

The organic phase is separated and concentrated under reduced pressure (approximately 8 mm of mercury).

Crystallization from ethanol makes it possible to isolate the benzophenone N-p-chlorophenylhydrazone in the form of pale yellow crystals, with a yield of 97%.

EXAMPLE 13

11.2 g of sodium hydroxide (1.4 eq; 0.28 mol), 31.40 g of 4-bromobenzene (1 eq; 0.2 mol) and 39.4 g of benzophenone hydrazone (1 eq; 0.2 mol) in 180 ml of degassed tert-amyl alcohol are loaded into a 500 ml reactor surmounted by a condenser, a mechanical stirrer and a temperature sensor, and placed under an inert atmosphere.

44.9 mg of palladium acetate (0.1 mol %; 0.0002 mol) and 145.6 mg of 2-dicyclohexylphosphino-2-methylbiphenyl (0.0004 mol) in 20 ml of degassed xylene are loaded into a 100 ml Schlenk tube equipped with a magnetic stirrer and placed under an inert atmosphere.

After stirring for twenty minutes, the catalyst thus prepared is transferred into the reactor.

After stirring at 103° C. for one hour, the reaction mixture is hydrolyzed with 100 ml of water and 100 ml of xylene are added.

The organic phase is separated and concentrated under reduced pressure (approximately 8 mm of mercury).

Crystallization from ethanol makes it possible to isolate the benzophenone N-phenylhydrazone in the form of pale yellow crystals, with a yield of 95%.

EXAMPLE 14

11.2 g of sodium hydroxide (1.4 eq; 0.28 mol), 37.40 g of 4-bromoanisole (1 eq; 0.2 mol) and 39.4 g of benzophenone hydrazone (1 eq; 0.2 mol) in 180 ml of degassed tert-amyl alcohol are loaded into a 500 ml reactor surmounted by a condenser, a mechanical stirrer and a temperature sensor, and placed under an inert atmosphere.

44.9 mg of palladium acetate (0.1 mol %; 0.0002 mol) and 145.6 mg of 2-dicyclohexylphosphino-2-methylbiphenyl (0.0004 mol) in 20 ml of degassed xylene are loaded into a 100 ml Schlenk tube equipped with a magnetic stirrer and placed under an inert atmosphere.

After stirring for twenty minutes, the catalyst thus prepared is transferred into the reactor.

After stirring at 103° C. for one hour, the reaction mixture is hydrolyzed with 100 ml of water and 100 ml of xylene are added.

The organic phase is separated and concentrated under reduced pressure (approximately 8 mm of mercury).

Crystallization from ethanol makes it possible to isolate the benzophenone N-methoxyphenylhydrazone in the form of pale yellow crystals, with a yield of 87%.

EXAMPLE 15

Comparative 11.2 g of sodium hydroxide (1.4 eq; 0.28 mmol) milled beforehand, 34.2 g of 4-bromotoluene (1 eq; 0.2 mol) and 39.4 g of benzophenone hydrazone (1 eq; 0.2 mol) in 190 ml of xylene are loaded into a 500 ml reactor surmounted by a condenser, a mechanical stirrer and a temperature sensor, and placed under an inert atmosphere.

44.8 mg of palladium acetate (0.01 mol %; 0.0002 mol) and 145.6 mg of 2-dicyclohexylphosphino-2-methylbiphenyl (0.0004 mol) in 20 ml of xylene are loaded into a 100 ml Schlenk tube equipped with a magnetic stirrer and placed under an inert atmosphere.

After stirring for twenty minutes, the catalyst thus prepared is transferred into the reactor.

After stirring at 130° C. for 48 hours, no reaction product is detected (conversion=0%).

EXAMPLE 16

Comparative 11.2 g of sodium hydroxide (1.4 eq; 0.28 mmol) milled beforehand, 34.2 g of 4-bromotoluene (1 eq; 0.2 mol) and 39.4 g of benzophenone hydrazone (1 eq; 0.2 mol) in 190 ml of toluene are loaded into a 500 ml reactor surmounted by a condenser, a mechanical stirrer and a temperature sensor, and placed under an inert atmosphere.

44.8 mg of palladium acetate (0.01 mol %; 0.0002 mol) and 145.6 mg of 2-dicyclohexylphosphino-2-methylbiphenyl (0.0004 mol) in 20 ml of toluene are loaded into a 100 ml Schlenk tube equipped with a magnetic stirrer and placed under an inert atmosphere.

After stirring for twenty minutes, the catalyst thus prepared is transferred into the reactor.

After stirring at 110° C. for 24 hours, no reaction product is detected (conversion=0%).

EXAMPLE 17

628 mg of milled potassium hydroxide (1.4 eq; 11.2 mmol), 1.368 g of 4-bromotoluene (1 eq; 8 mmol) and 1.57 g of benzophenone hydrazone (1 eq; 8 mmol) in 7 ml of tert-butanol are loaded into a 20 ml reactor surmounted by a condenser, a magnetic stirrer and a temperature sensor, and placed under an inert atmosphere.

8.1 mg of palladium acetate and 26.1 mg of 2-dicyclohexylphosphino-2-methylbiphenyl in 7 ml of tert-butanol are loaded into a 5 ml Schlenk tube equipped with a magnetic stirrer and placed under an inert atmosphere.

After stirring for twenty minutes, the catalyst (0.005 eq; 0.5 mol %; 1 ml) is transferred into the reactor.

After stirring at 90° C. for eight hours, the conversion of the 4-bromotoluene is complete and a benzophenone N-tolylhydrazone yield of 78% is measured by gas chromatography in the presence of an internal standard (hexacosane).

EXAMPLE 18

Comparative 1.256 g of potassium tert-butoxide (1.4 eq; 11.2 mmol), 1.368 g of 4-bromotoluene (1 eq; 8 mmol) and 1.57 g of benzophenone hydrazone (1 eq; 8 mmol) in 7 ml of tert-butanol are loaded into a 20 ml reactor surmounted by a condenser, a magnetic stirrer and a temperature sensor, and placed under an inert atmosphere.

8.1 mg of palladium acetate and 26.1 mg of 2-dicyclohexylphosphino-2-methylbiphenyl in 7 ml of tert-butanol are loaded into a 5 ml Schlenk tube equipped with a magnetic stirrer and placed under an inert atmosphere.

After stirring for twenty minutes, the catalyst (0.005 eq; 0.5 mol %; 1 ml) is transferred into the reactor.

After stirring at 90° C. for 48 hours, there is zero conversion of the 4-bromotoluene.

EXAMPLE 19

6.6 g of milled sodium hydroxide (1.1 eq; 0.165 mol), 30 g of 5-bromo-2-fluorocyanobenzene (1 eq; 0.15 mol) and 29.4 g of benzophenone hydrazone (1 eq; 0.15 mol) in 190 ml of degassed tert-amyl-alcohol are loaded into a 500 ml reactor surmounted by a condenser, a mechanical stirrer and a temperature sensor, and placed under an inert atmosphere.

168 mg of palladium acetate (0.001 mol %; 0.00075 mol) and 867 mg of 4,5-bis(diphenylphosphino)-9,9-dimethylxanthene (0.0015 mol) in 20 ml of degassed tert-amyl alcohol are loaded into a 100 ml Schlenk tube equipped with a magnetic stirrer and placed under an inert atmosphere.

After stirring for twenty minutes, the catalyst thus prepared is transferred into the reactor.

After stirring at 103° C. for 12 hours, the reaction mixture is hydrolyzed with 100 ml of water and the organic phase is separated.

Direct crystallization from tert-amyl alcohol makes it possible to isolate the corresponding benzophenone N-4-fluoro-3-cyanophenylhydrazone with a quantitative yield.

EXAMPLE 20

448 mg of milled sodium hydroxide (1.4 eq; 0.0112 mmol), 1.32 g of 1,3-dichloro-4-fluorobenzene (1 eq; 0.008 mol) and 1.57 g of benzophenone hydrazone (1 eq; 0.008 mol) in 6 ml of degassed tert-amyl alcohol are loaded into a 20 ml reactor surmounted by a condenser, a mechanical stirrer and a temperature sensor, and placed in an inert atmosphere.

8.95 mg of palladium acetate (0.001 mol %; 0.00004 mol) and 46.3 mg of 4,5-bis(diphenylphosphino)-9,9-dimethylxanthene (0.0008 mol) in 2 ml of degassed tert-amyl alcohol are loaded into a 100 ml Schlenk tube equipped with a magnetic stirrer and placed under an inert atmosphere.

After stirring for twenty minutes, the catalyst thus prepared is transferred into the reactor.

After stirring at 103° C. for 12 hours, the conversion of the 1,3-dichloro-4-fluorobenzene is complete and a benzophenone N-5-chloro-2-fluorophenylhydrazone yield of 85% (accompanied by 15% of benzophenone N-3-chloro-4-fluorophenylhydrazone) is measured by gas chromatography in the presence of an internal standard (hexacosane).

EXAMPLE 21

448 mg of milled sodium hydroxide (1.4 eq; 0.0112 mmol), 1.67 g of 4-bromo-2-chloro-1-fluorobenzene (1 eq; 0.008 mol) and 1.57 g of benzophenone hydrazone (1 eq; 0.008 mol) in 6 ml of degassed tert-amyl alcohol are loaded into a 20 ml reactor surmounted by a condenser, a mechanical stirrer and a temperature sensor, and placed under an inert atmosphere.

8.95 mg of palladium acetate (0.001 mol %; 0.00004 mol) and 46.3 mg of 4,5-bis(diphenylphosphino)-9,9-dimethylxanthene (0.0008 mol) in 2 ml of degassed tert-amyl alcohol are loaded into a 100 ml Schlenk tube equipped with a magnetic stirrer and placed under an inert atmosphere.

After stirring for twenty minutes, the catalyst thus prepared is transferred into the reactor.

After stirring at 103° C. for 12 hours, the conversion of the 4 bromo-2-chloro-1-fluorobenzene is complete.

The reaction mixture is hydrolyzed with 10 ml of water and the organic phase is separated.

Direct crystallization from tert-amyl alcohol makes it possible to isolate the corresponding benzophenone N-3-chloro-4-fluorophenylhydrazone with a yield of 83%.

EXAMPLE 22

11.2 g of sodium hydroxide and 50 ml of tert-amyl alcohol are loaded into a 150 ml blade mill, and mixing is carried out until a homogeneous suspension of sodium hydroxide in the alcohol is obtained.

The suspension of sodium hydroxide in alcohol prepared beforehand, 34.2 g of 4-bromotoluene (1 eq; 0.2 mol) and 39.4 g of benzophenone hydrazone (1 eq; 0.2 mol) in 140 ml of tert-amyl alcohol are loaded into a 500 ml reactor surmounted by a condenser, a mechanical stirrer and a temperature sensor, and placed under an inert atmosphere.

4.48 mg of palladium acetate (0.01 mol %; 0.00002 mol) and 14.56 mg of 2-dicyclohexylphosphino-2-methylbiphenyl (0.02 mol %; 0.00004 mol) in 10 ml of xylene are loaded into a 100 ml Schlenk tube equipped with a magnetic stirrer and placed under an inert atmosphere.

After stirring for twenty minutes, the catalyst thus prepared is transferred into the reactor.

After stirring at 103° C. for 7 hours, the conversion of the 4-bromotoluene is complete and a benzophenone N-p-tolylhydrazone yield of 91% is measured by gas chromatography in the presence of an internal standard (hexacosane).

The invention claimed is:

1. A method of creating a carbon-heteroatom bond by reacting a leaving group-bearing unsaturated compound and a nucleophilic compound introducing a heteroatom which can substitute for the leaving group, thereby creating a carbon-heteroatom bond, in the presence of a palladium-based catalyst, said reaction taking place in the presence of an effective amount of a metal hydroxide or ammonium hydroxide, with an alcohol solvent, wherein said leaving group-bearing unsaturated compound is an aromatic compound subsequently referred to as "haloaromatic compound" and that can be represented by formula (IIc):

wherein:
D is a benzene ring,
$R_{23}$, which is identical or different, represent substituents on the ring,
Y represents a leaving group,
n'' represents the number of substituents on the ring, and wherein said nucleophilic compound is a hydrazone.

2. The method as claimed in claim 1, wherein the nucleophilic compound corresponds to the formula below:

wherein:
$R_{12}$, $R_{13}$ and $R_{14}$, which are identical or different, represent, independently of one another, a hydrogen atom or a hydrocarbon group having from 1 to 20 carbon atoms,
at most one of the groups $R_{12}$ and $R_{13}$ represents a hydrogen atom, or
else $R_{12}$ and $R_{13}$ are linked so as to constitute, with the carbon atoms that bear them, a monocyclic or polycyclic, saturated, unsaturated or aromatic, carbocyclic or heterocyclic group having from 3 to 20 atoms.

3. The method as claimed in claim 1, wherein the nucleophilic compound is benzophenone hydrazone.

4. The method as claimed in claim 1, wherein the leaving group-bearing compound is p-chlorotoluene, p-bromoanisole or p-bromotrifluorobenzene.

5. The method as claimed in claim 1, wherein the catalyst comprises the metal element Pd introduced in the form of a finely divided metal, in the form of an inorganic derivative; in the form of a mineral salt, in the form of an organic derivative, or in the form of a complex.

6. The method as claimed in claim 5, wherein the Pd element is introduced through palladium chloride, palladium acetate or palladium-on-charcoal.

7. The method as claimed in claim 1, wherein the ligand is a phosphine, a phosphite or a phosphonite.

8. The method as claimed in claim 7, wherein the phosphine corresponds to the formula below:

(IIIa)

in said formula:
q is equal to 0 or 1,
the groups $R_a$, $R_b$, $R_c$ and $R_d$, which are identical or different, represent:
an alkyl group having from 1 to 12 carbon atoms,
a cycloalkyl group having 5 or 6 carbon atoms,
a cycloalkyl group having 5 or 6 carbon atoms, which is substituted with one or more alkyl groups having 1 to 4 carbon atoms, or alkoxy groups having 1 or 4 carbon atoms,
a phenylalkyl group in which the aliphatic portion contains from 1 to 6 carbon atoms,
a phenyl or biphenyl group,
a phenyl or biphenyl group substituted with one or more alkyl groups having from 1 to 4 carbon atoms or alkoxy groups having from 1 to 4 carbon atoms, one or more halogen atoms, or a trifluoromethyl group,
the group $R_e$ represents:
a valency bond or a saturated or unsaturated, linear or branched divalent hydrocarbon group having from 1 to 6 carbon atoms,
an aromatic group of formula:

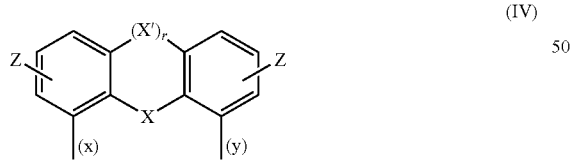

(IV)

in which:
Z represents a hydrogen atom, an alkyl group having from 1 to 10 carbon atoms, a halogen atom or a trifluoromethyl group,
X is an oxygen or sulfur atom or a linear or branched alkylene group having from 1 to 3 carbon atoms,
if r is equal to 1, X' represents a valency bond, an oxygen, sulfur or silicon atom or a linear or branched alkylene group having from 1 to 3 carbon atoms,
if r is equal to 0, the two rings are not linked,
(x) and (y) pinpoint respectively the two bonds established between the group $R_e$ symbolized by formula (IV) and the phosphorus atoms,
an aromatic group of formula:

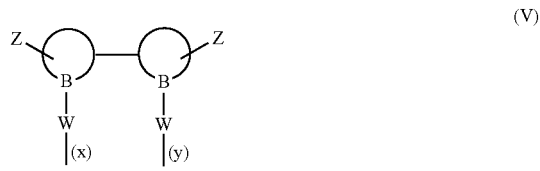

(V)

in which:
Z has the meaning given above,
B represents the residue of a benzene or naphthalene ring,
W represents a valency bond or a linear or branched alkylene group having from 1 to 3 carbon atoms,
(X) and (y) pinpoint respectively the two bonds established between the group $R_e$ symbolized by formula (V) and the phosphorus atoms,
a ferrocene group of formula:

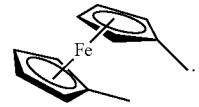

9. A method as claimed in claim 7, wherein the phosphine corresponds to the formula below:

(IIIb)

in which:
C represents the residue of a pentane or cyclohexane ring,
$R_f$ and $R_g$, which may be identical or different, represent:
an alkyl group having from 1 to 12 carbon atoms,
a cycloalkyl group having 5 or 6 carbon atoms,
a cycloalkyl group having 5 or 6 carbon atoms, which is substituted with one or more alkyl groups having 1 to 4 carbon atoms, or alkoxy groups having 1 or 4 carbon atoms,
a phenylalkyl group in which the aliphatic portion contains from 1 to 6 carbon atoms,
a phenyl or biphenyl group,
a phenyl or biphenyl group substituted with one or more alkyl groups having from 1 to 4 carbon atoms or alkoxy groups having from 1 to 4 carbon atoms, one or more halogen atoms, or a trifluoromethyl group, and
s is a number equal to 1 to 6.

10. The method as claimed in claim 7, wherein the phosphonite corresponds to the formula below:

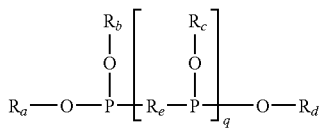

(IIIc)

in said formula:
q is equal to 0 or 1,
the groups $R_a$, $R_b$, $R_c$ and $R_d$, which are identical or different, represent:
an alkyl group having from 1 to 12 carbon atoms,
a cycloalkyl group having 5 or 6 carbon atoms,
a cycloalkyl group having 5 or 6 carbon atoms, which is substituted with one or more alkyl groups having 1 to 4 carbon atoms, or alkoxy groups having 1 or 4 carbon atoms,
a phenylalkyl group in which the aliphatic portion contains from 1 to 6 carbon atoms,
a phenyl or biphenyl group,
a phenyl or biphenyl group substituted with one or more alkyl groups having from 1 to 4 carbon atoms or alkoxy groups having from 1 to 4 carbon atoms, one or more halogen atoms, or a trifluoromethyl group,
the group $R_e$ represents:
a valency bond or a saturated or unsaturated, linear or branched divalent hydrocarbon group having from 1 to 6 carbon atoms,
an aromatic group of formula:

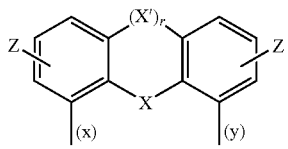

(IV)

in which:
Z represents a hydrogen atom, an alkyl group having from 1 to 10 carbon atoms, a halogen atom or a trifluoromethyl group,
X is an oxygen or sulfur atom or a linear or branched alkylene group having from 1 to 3 carbon atoms,
if r is equal to 1, X' represents a valency bond, an oxygen, sulfur or silicon atom or a linear or branched alkylene group having from 1 to 3 carbon atoms,
if r is equal to 0, the two rings are not linked,
(x) and (y) pinpoint respectively the two bonds established between the group $R_e$ symbolized by formula (IV) and the phosphorus atoms,
an aromatic group of formula:

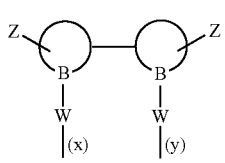

(V)

in which:
Z has the meaning given above,

B represents the residue of a benzene or naphthalene ring,
W represents a valency bond or a linear or branched alkylene group having from 1 to 3 carbon atoms,
(x) and (y) pinpoint respectively the two bonds established between the group $R_e$ symbolized by formula (V) and the phosphorus atoms,
a ferrocene group of formula:

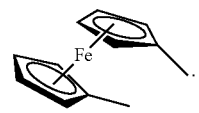.

11. The method as claimed in claim 7, wherein the ligand is: tricyclohexylphosphine, trimethylphosphine, triethylphosphine, tri-n-butylphosphine, triisobutylphosphine, tri-tert-butylphosphine, tribenzylphosphine, dicyclohexylphenylphosphine, 2-dicyclohexylphosphino-2-methylbiphenyl, triphenylphosphine, dimethylphenylphosphine, diethylphenylphosphine, di-tert-butylphenylphosphine, tri(p-tolyl)phosphine, isopropyldiphenylphosphine, tris(pentafluorophenyl)phosphine, tri(o-tolyl)phosphine, bisdiphenylphosphinomethane, bisdiphenylphosphinoethane, bisdiphenylphosphinopropane, bisdiphenylphosphinobutane, bisdiphenylphosphinopentane, bisdiphenylphosphinoferrocene, 2,2'-bis(diphenylphosphino)-1,1'-binaphthyl (BINAP), bis-[(2-diphenylphosphino)phenyl] ether (DPEPHOS), 4,5-bis(diphenylphosphino)-9,9-dimethylxanthene (XANTPHOS), or tetrakis-(2,4-di-tert-butylphenyl)-4,4'-diphenylenebisphosphonite.

12. The method as claimed in claim 1, wherein the base is an ammonium hydroxide or a hydroxide of a monovalent metal and/or of a bivalent metal, introduced in a solid form or in a solution.

13. The method as claimed in claim 1, wherein the solvent is a monoalcohol, a polyalcohol, an ether alcohol or an amino alcohol.

14. The method as claimed in claim 13, wherein the alcohol is a is a primary alcohol or secondary alcohol that is hindered or a tertiary alcohol, said alcohol corresponds to the formula below:

$$R_h\text{—OH} \quad (VI)$$

in said formula (VI):
$R_h$ represents an optionally substituted hydrocarbon group having from 1 to 24 carbon atoms, which is a linear or branched, saturated or unsaturated acyclic aliphatic group; a monocyclic or polycyclic, saturated or unsaturated cycloaliphatic group; or a linear or branched, saturated or unsaturated aliphatic group bearing a cyclic substituent.

15. The method as claimed in claim 14, wherein the solvent is n-butanol, tert-butanol, ethylene glycol, N,N-dimethylethanolamine; methoxy-ethanol, 1-methoxypropan-2-ol, or tert-amyl alcohol.

16. The method as claimed in claim 12, wherein a reactive milling of the metal hydroxide or ammonium hydroxide and of the alcohol is carried out.

17. The method as claimed in claim 12, wherein a reactive milling of sodium hydroxide (already milled or in the form of pellets) and of tert-amyl alcohol or tert-butanol is carried out.

18. The method as claimed in claim 1, wherein the compound introducing the Pd element, is used in an amount, expressed by the molar ratio of the number of moles of said Pd compound to the number of moles of compound of formula (IIc), ranges between 0.005 and 1.

19. The method as claimed in claim 1, wherein the alcohol-type solvent is further combined with a co-solvent which is an apolar aprotic solvent.

20. The method as claimed in claim 19, wherein the apolar aprotic solvent is an aliphatic, cycloaliphatic or aromatic hydrocarbon.

21. The method as claimed in claim 19, wherein the co-solvent is used in an amount representing from 1 to 50% of the volume of the alcohol solvent.

22. The method as claimed in claim 1, wherein the coupling reaction between the nucleophilic compound and the leaving group-bearing unsaturated compound takes place at a temperature which is chosen such that the reactants are maintained in the liquid state.

23. The method as claimed in claim 22, wherein the temperature is situated between 50° C. and 200° C.

24. The method as claimed in claim 1, wherein the leaving group-bearing unsaturated compound, the base, the alcohol solvent are loaded; the compound introducing the Pd metal element and the ligand or else the preformed metal complex are added separately to the medium; the reaction medium is brought to the selected reaction temperature; the nucleophilic compound, is subsequently added and the coupling product obtained is then recovered.

25. The method as claimed in claim 1, wherein the coupling product obtained is benzophenone N-p-tolylhydrazone, benzophenone N-phenylhydrazone, benzophenone N-p-methoxyphenylhydrazone, benzophenone N-o-tolylhydrazone, benzophenone N-p-fluorophenylhydrazone, benzophenone N-4-fluoro-3-chlorophenylhydrazone, benzophenone N-2-fluoro-5-chlorophenylhydrazone, or benzophenone N-4-fluoro-3-cyanophenylhydrazone.

26. The method of claim 1, wherein the palladium-based catalyst is a ligand.

27. The method of claim 1, wherein the leaving group represented by Y is a halogen atom or a sulfonic ester group of formula —$OSO_2$—$R_e$, in which $R_e$ is a hydrocarbon group.

28. The method of claim 2, wherein the hydrocarbon group having from 1 to 20 carbon atoms is a linear or branched, saturated or unsaturated, acyclic aliphatic group; a monocyclic or polycyclic, saturated, unsaturated or aromatic carbocyclic or heterocyclic group; or a chain of the abovementioned groups.

29. The method of claim 5, wherein mineral salt is a nitrate, a sulfate, an oxysulfate, a halide, an oxyhalide or a carbonate.

30. The method of claim 5, wherein the organic derivative is a cyanide, an oxalate, an acetylacetonate, an alkoxide, a methoxide, an ethoxide, a carboxylate, or an acetate.

31. The method of claim 5, wherein the complex is a chlorinated or cyanated complex of Pd metals, of alkali metals, of Pd and alkali metals, or of ammonium.

32. The method of claim 31, wherein the alkali metal is sodium or potassium.

33. The method of claim 12, wherein the bivalent metal is an alkali earth metal, an alkaline earth metal, or combinations thereof.

34. The method of claim 18, wherein the amount ranges between 0.01 and 0.1.

35. The method of claim 20, wherein the aliphatic hydrocarbon is a hexane, a cyclohexane, a methylcyclohexane, or petroleum ether cuts.

36. The method of claim 20 wherein the aromatic hydrocarbon is benzene, toluene, xylenes, cumene, mesitylene, or petroleum cuts consisting of a mixture of alkylbenzenes.

37. The method of claim 21, wherein the co-solvent is used in an amount representing 10 to 20% of the volume of the alcohol solvent.

38. The method of claim 23, wherein the temperature is situated between 90° C. and 110° C.

* * * * *